United States Patent [19]
DeLong et al.

[11] 3,937,822
[45] Feb. 10, 1976

[54] METHOD FOR TREATING PSORIASIS

[75] Inventors: Donald C. DeLong; Koert Gerzon, both of Indianapolis, Ind.

[73] Assignee: Eli Lilly and Company, Indianapolis, Ind.

[22] Filed: July 22, 1974

[21] Appl. No.: 490,626

[52] U.S. Cl. .................................................. 424/181
[51] Int. Cl.² ........................................... A61K 31/71
[58] Field of Search ..................................... 424/181

[56] References Cited
UNITED STATES PATENTS 3,674,774   7/1972   Williams et al. .................... 424/180

*Primary Examiner*—Jerome D. Goldberg
*Attorney, Agent, or Firm*—Charles W. Ashbrook; Everet F. Smith

[57] ABSTRACT

Psoriasis is treated topically, orally or parenterally with pyrazofurin.

5 Claims, No Drawings

METHOD FOR TREATING PSORIASIS

BACKGROUND OF THE INVENTION

Psoriasis is a chronic inflammatory skin disease of unknown cause, characterized by the development of reddish patches of skin covered with silvery-white imbricated scales. The disease generally affects the extensor surfaces of the body, along with the back and the scalp. It is believed that the disease is determined in part by a genetically dominant trait. Psoriasis is generally not seen at birth, but can begin at any age from early childhood to extreme old age, and is normally most severe between the ages of 10 and 50. The disease does not appear to be communicable, and environmental causes are not apparent. Factors often influencing psoriasis include local trauma, preceding mild inflammatory diseases, psychosomatic factors, and climate, especially low relative humidity.

While several treatments are currently available for psoriasis, no therapeutic method assures a cure. Prolonged use of any agent usually reduces its effectiveness. Agents commonly used in treating psoriasis include coal tar, ammoniated mercury, anthralin, and topical corticosteroids such as fluocinolone acetonide, fluorandrenolide, and triamcinolone acetonide. Methotrexate has been used systemically in the treatment of severe and extensive psoriasis; however, its extreme toxicity is generally a limiting factor in its use. Antimetabolite drugs such as aminopterin, thioguanine, and Azaribine have also been used.

Extensive research has been directed toward finding better methods of treatment, and even potential cures, for psoriasis. An effective topical treatment would be especially useful and desirable. Comaish and Juhlin have indicated that while methotrexate is useful in treating psoriasis systemically, it is not successful when used topically; *Arch. Dermatol.*, 100, 99 (1969). Only one antimetabolite, fluorouracil, has been claimed to be topically effective against psoriasis; *Z. Haut. Geschlechtskrankh*, 44, 361 (1969).

Pyrazofurin is a C-nucleoside antimetabolite obtained initially by fermentation of a strain of *Streptomyces candidus*. The isolation and characterization of pyrazofurin is described in detail in U.S. Pat. No. 3,674,774. The generic name pyrazofurin replaces the generic name pyrazomycin in accordance with nomenclature adopted by the United States Adopted Names Council. This C-nucleoside has demonstrated utility as an antifungal and antibacterial agent. In accordance with this invention, pyrazofurin is useful in treating psoriasis, and is especially useful when applied topically due to its almost complete topical absorption properties.

It is an object of the present invention to provide a new and improved method for treating psoriasis, which method comprises administering pyrazofurin to a patient afflicted with the disease, the administration being either topical, oral, or parenteral, or by a combination of these routes.

SUMMARY OF THE INVENTION

This invention relates to a new and improved method of treating psoriasis. In particular, this invention provides a method of treating psoriasis comprising administering to a subject suffering from psoriasis and in need of treatment an effective amount of pyrazofurin, which compound has the formula

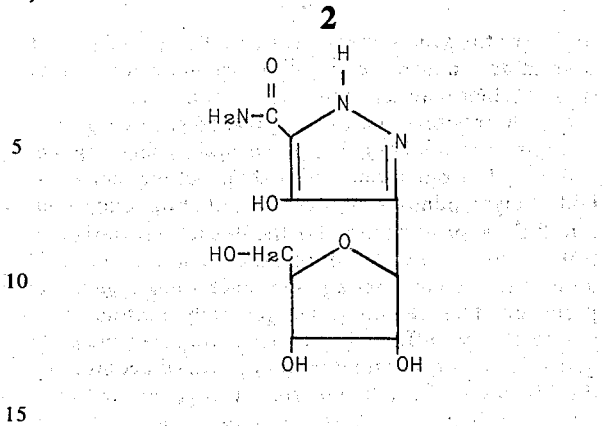

According to the invention, the compound of the above formula is administered to a patient suffering from psoriasis by the topical, oral, or parenteral route.

DETAILED DESCRIPTION OF THE INVENTION

Pyrazofurin is a C-nucleoside having the above formula and is systematically named 4-hydroxy-3$\beta$-D-ribofuranosylpyrazole-5-carboxamide. According to this invention, pyrazofurin is administered to a patient suffering from psoriasis and in need of treatment. The preferred route of administration, mainly because of simplicity of use and because of the unique topical absorption properties of pyrazofurin, is by topical application. The preferred method of treatment comprises applying an effective amount of a compound of the above formula directly to the psoriatic lesion. Generally, the compound is formulated for topical application as an ointment or as a solution. Ointments and solutions for topical administration can be formulated with any of a number of pharmaceutically acceptable carriers, including animal and vegetable oils, mixtures of waxes, solid and liquid hydrocarbons, glycols, and the like. A typical ointment composition for treating psoriasis according to this invention, for example, comprises the following ingredients per gram of ointment:

|  | mg. |
|---|---|
| Pyrazofurin | 1–50 |
| Polyethylene glycol 300 (N.F.) | 500–700 |
| Polyethylene glycol 4000 (U.S.P.) | 299–450 |

A typical solution containing the compound of the above formula and being of a suitable formulation for topical administration comprises the following:

|  | mg. |
|---|---|
| Pyrazofurin | 1–50 |
| Glycerine (U.S.P.) | 950–999 |

In carrying out the novel method of treating psoriasis provided herein, pyrazofurin is formulated as a suitable ointment or solution, such as that described hereinabove for example, and the ointment or solution is administered directly to a psoriatic lesion at a rate of about 25 to about 125 mcg. per square cm. of skin surface once every 1 to 4 days until the disease is controlled. Generally, the ointment or solution is applied to the affected skin area for a period of time necessary to relieve the symptoms of psoriasis. Prolonged periods of treatment may be required in cases of severe psoriasis and when maintenance therapy is desired.

As hereinbefore indicated, pyrazofurin can also be administered orally. The general oral dosage regimen will include from about 0.5 to about 12 mg. per kg. of body weight, administered at a rate of about once every 3 to 8 days, or as needed for the desired psoriasis control, up to the level of intolerance if any is noted. A dose of about 3 mg. per kg. once each week is generally preferred. The treatment will generally continue for a period of time sufficient to achieve control of the psoriatic lesions. For oral treatment of psoriasis according to this invention, the active ingredient is generally formulated in tablets, in gelatin capsules, or in solution or suspension with a suitable diluent or carrier. Suitable pharmaceutical diluents or carriers include lactose, sucrose, starch powder, cellulose, calcium sulfate, sodium benzoate, and the like. A typical tablet formulation, for example, may consist of the following ingredients:

|  | mg. |
|---|---|
| Pyrazofurin | 350 |
| Lactose | 250 |
| Starch powder | 250 |
| Dicalcium phosphate anhydrous | 100 |
| Stearic acid | 25 |
| Magnesium stearate | 25 |

A suitable empty telescopying gelatin capsule for oral administration will contain from about 50 to about 500 mg. of pyrazofurin, admixed with a suitable diluting substance, such as starch for example, in the amount of about 500 mg. Such a capsule would be administered about once every 3 to 15 days, both for therapeutic as well as maintenance control of psoriasis.

In the case of parenteral administration, pyrazofurin is formulated with any of a number of pharmaceutically acceptable carriers to constitute an injectable liquid solution. Typical carriers include water or saline solutions, or suitable buffered aqueous solutions. Aromatic alcohols, such as phenol, can also be added to the solution for stabilization if desired. Generally, the drug will be dissolved in water, buffered to a neutral solution and lyophilized to a dry powder, ready for reconstitution by the addition of water when needed. A preferred route of parenteral administration when treating psoriasis according to this invention is the intravenous route. A dosage regimen will consist of administering pyrazofurin in the amount of about 0.1 to about 10 mg. per kg. of body weight at intervals of every 3 to 8 days. Generally, a dose of about 3 to 5 mg. per kg. per week administered intravenously will be sufficient to promote improvement of psoriatic lesions. Toxic effects, such as stomatitis or diarrhea, may be observed in some patients with higher dose regimens. Maintenance therapy can be accomplished by a reduced dosage regimen adjusted to the individual requirements of the particular patient being treated.

As hereinbefore indicated, pyrazofurin is a known coupound, obtained initially by fermentation of a strain of *Streptomyces candidus*. The isolation and characterization of pyrazofurin (pyrazomycin) is described in detail in U.S. Pat. No. 3,674,774.

Pyrazofurin is an antimetabolite which appears to have the same biological mode of action as does 6-azauridine and 2',3',5'-tri-O-acetyl-6-azauridine. In particular, all of these drugs are converted to the corresponding 5'-phosphate ester in the animal organism. The biological action of the 5'-phosphate ester is thought to depend upon the interference with the biosynthesis of pyrimidine precursors of nucleic acids by the inhibition of the activity of orotidylic acid decarboxylase. The biological actions of antimetabolites is discussed in detail by Plevova et al., *Biochem. Pharmacol.*, 20, 2071 (1971); and Pasternak et al., *J. Biol. Chem.*, 234, 2992 (1959).

Pyrazofurin can be administered to a human afflicted with psoriasis and in need of treatment. The novel process provided herein for treating psoriasis consists of oral, topical, or parenteral administration of the antipsoriatic agent. In the case of topical treatment, an effective amount of pyrazofurin is applied directly to the psoriatic lesion. When psoriasis is treated orally according to the invention, pyrazofurin is administered orally in the form of a tablet or capsule or as a liquid solution or suspension. In the case of parenteral treatment of psoriasis, the route most preferred is the intravenous route.

We claim:
1. The method of treating psoriasis in humans comprising the administration to a patient suffering from psoriasis an effective dose for treating psoriasis of a compound having the formula

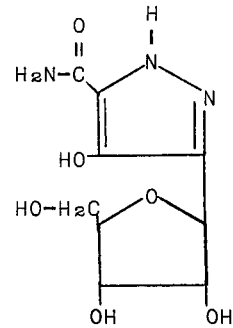

2. The method of claim 1, wherein the compound is administered topically.
3. The method of claim 1, wherein the compound is administered orally.
4. The method of clam 1, wherein the compound is administered parenterally.
5. The method of claim 4, wherein the compound is administered intravenously.

* * * * *